United States Patent [19]

Haacke et al.

[11] Patent Number: 4,678,996
[45] Date of Patent: Jul. 7, 1987

[54] MAGNETIC RESONANCE IMAGING METHOD

[75] Inventors: E. Mark Haacke, University Heights; Francis H. Bearden, Twinsburg, both of Ohio

[73] Assignee: Picker International, Inc., Highland Hts., Ohio

[21] Appl. No.: 731,509

[22] Filed: May 7, 1985

[51] Int. Cl.⁴ .......................................... G01R 33/20
[52] U.S. Cl. .................................. 324/309; 324/312
[58] Field of Search ............... 324/309, 307, 312, 313, 324/314, 311

[56] References Cited

U.S. PATENT DOCUMENTS

| | | | |
|---|---|---|---|
| 4,070,611 | 1/1978 | Ernst | 324/309 |
| 4,165,479 | 8/1979 | Mansfield | 324/309 |
| 4,307,343 | 12/1981 | Likes | 324/309 |
| 4,354,157 | 10/1982 | Feiner | 324/312 |
| 4,355,282 | 10/1982 | Young et al. | 324/309 |
| 4,451,788 | 5/1984 | Edelstein et al. | 324/309 |
| 4,509,015 | 4/1985 | Ordidge et al. | 324/309 |
| 4,527,124 | 7/1985 | Van Uijen | 324/309 |
| 4,588,948 | 5/1986 | Mansfield | 324/309 |
| 4,595,879 | 6/1986 | Lent et al. | 324/309 |

FOREIGN PATENT DOCUMENTS

| | | | |
|---|---|---|---|
| 0127480 | 12/1984 | European Pat. Off. | 324/309 |
| 2125563 | 3/1984 | United Kingdom | 324/309 |

OTHER PUBLICATIONS

"The K-Trajectory Formulation of the NMR Imaging Process with Applications in Analysis and Synthesis of Imaging Methods", Donald B. Twieg, Med. Phys., 10(5), Sep./Oct. 1983.
"A Simple Graphical Representation of Fourier-Based Imaging Methods", Stig Ljunggren, J. Mag. Resonance, 54, 338 (1983).
"Improvements in Performance Time for Simultaneous Three-Dimensional NMR Imaging", G. Johnson et al., J. Mag. Resonance, 54, 374-384 (1983).
"Rapid Data-Acquisition Technique for NMR Imaging by the Projection-Reconstruction Method", Laurence D. Hall et al., J. Mag. Resonance, 56, 179-182 (1984).
"Biological and Medical Imaging by NMR", P. Mansfield et al., J. Mag. Resonance, 29, 355-373 (1978).
"A Unified Description of NMR Imaging, Data-Collection Strategies, and Reconstruction", Kevin F. King, Med. Phys., 11(1), Jan./Feb. 1984.
"Image Reconstruction for the NMR Echo-Planar Technique, and for a Proposed Adaptation to Allow Continuous Data Acquisition", J. Mag. Resonance, 42, 193-202 (1981).
"Fast Fourier Imaging", C. M. J. Van Uijen et al., Mag. Resonance in Medicine, vol. 1, No. 2, Jun. 1984.

Primary Examiner—Stewart J. Levy
Assistant Examiner—Scott M. Oldham
Attorney, Agent, or Firm—Fay, Sharpe, Beall, Fagan, Minnich & McKee

[57] ABSTRACT

Hybrid fast scan magnetic resonance imaging is performed by using, for example, both a two dimensional Fourier transform (2DFT) method using phase encoding prior to data collection and an echo planar technique which phase encodes by using an oscillating gradient during data collection. In this hybrid imaging, the amplitude of the oscillating gradient determines the time savings achieved in imaging. The hybrid scan has particular application for medical diagnostic imaging since it is advantageous that such imaging be conducted as rapidly as possible.

30 Claims, 16 Drawing Figures

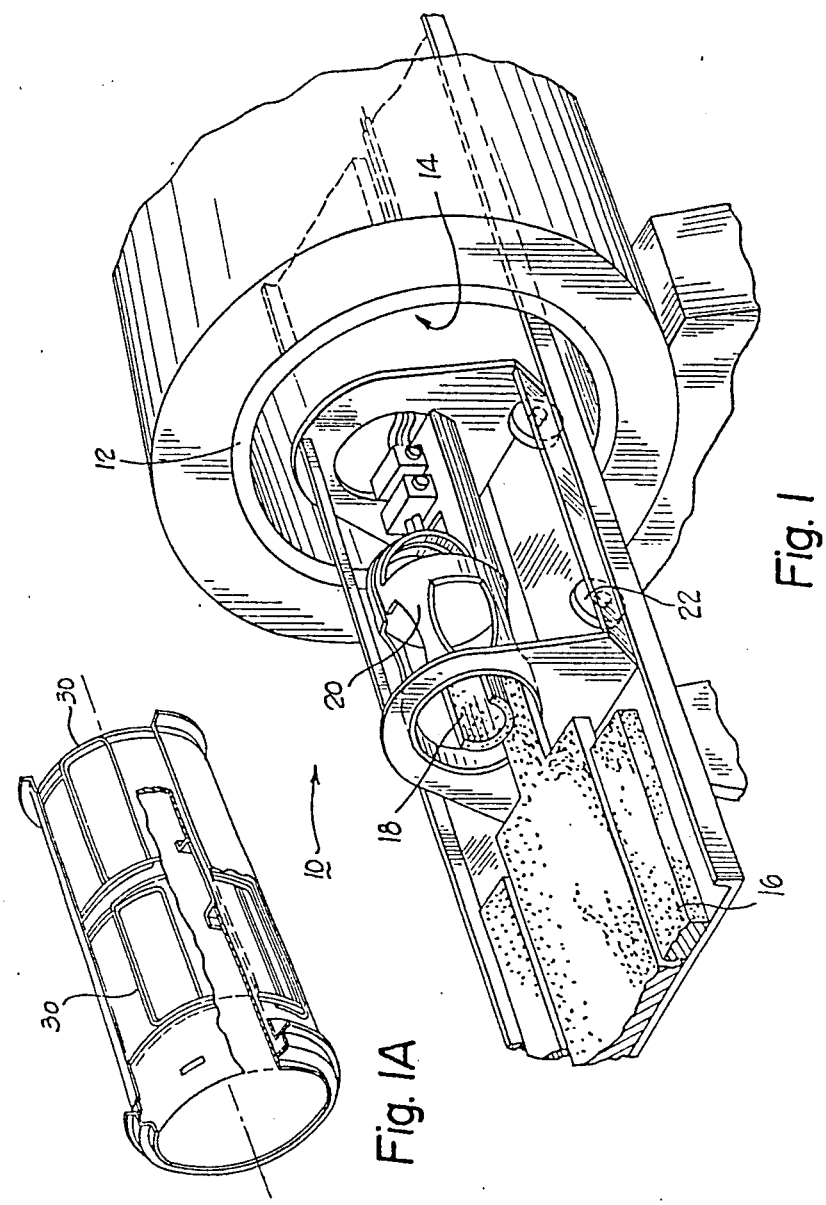

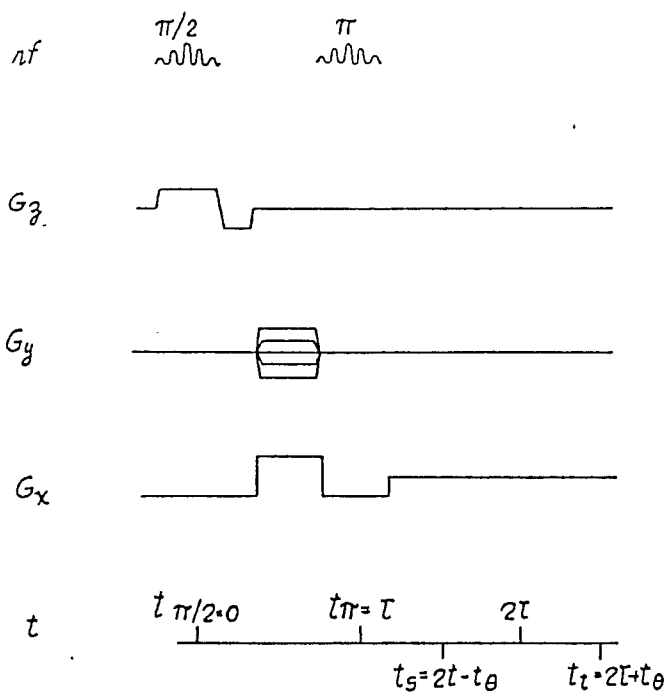
PRIOR ART  Fig. 2
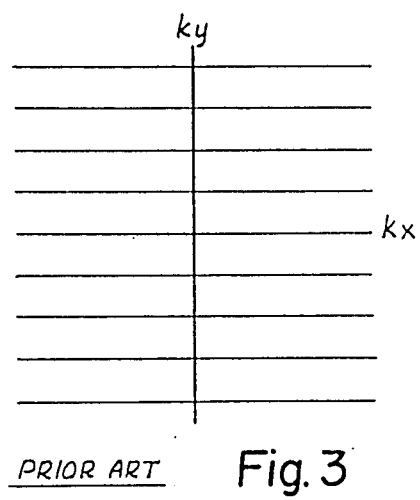
PRIOR ART  Fig. 3

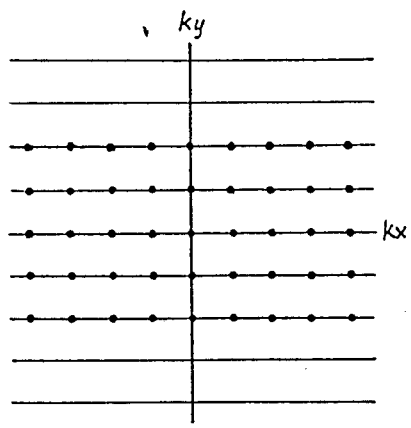
PRIOR ART
Fig. 4
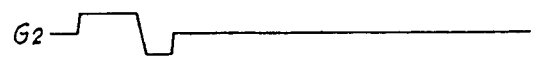
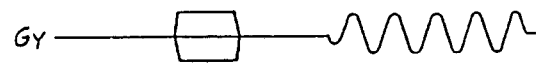
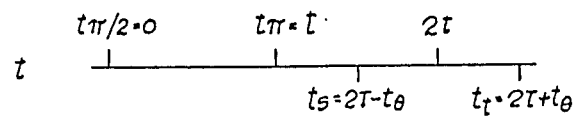
Fig. 5

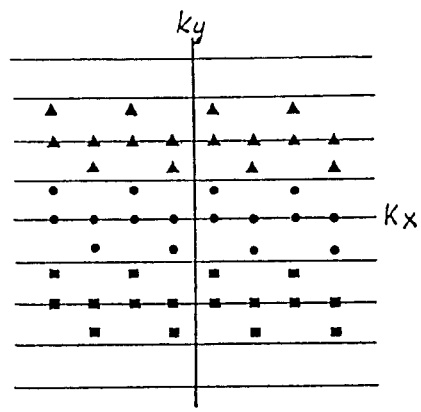
Fig. 10
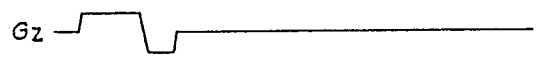
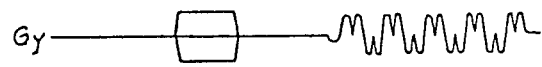
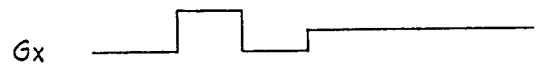
Fig. 11

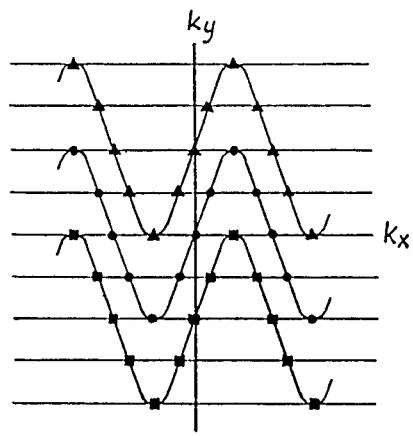
Fig. 12
rf  π/2    π
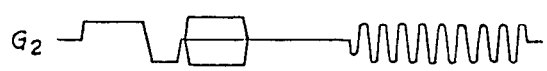
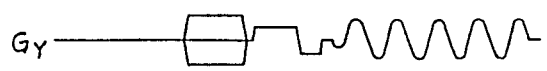
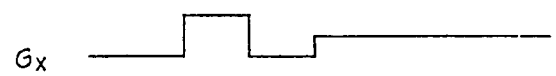
$t$  $t_{\pi/2}=0$   $t_\pi=T$   $2T$
              $t_s=2T-t_\theta$   $t_t=2T+t_\theta$
Fig. 13

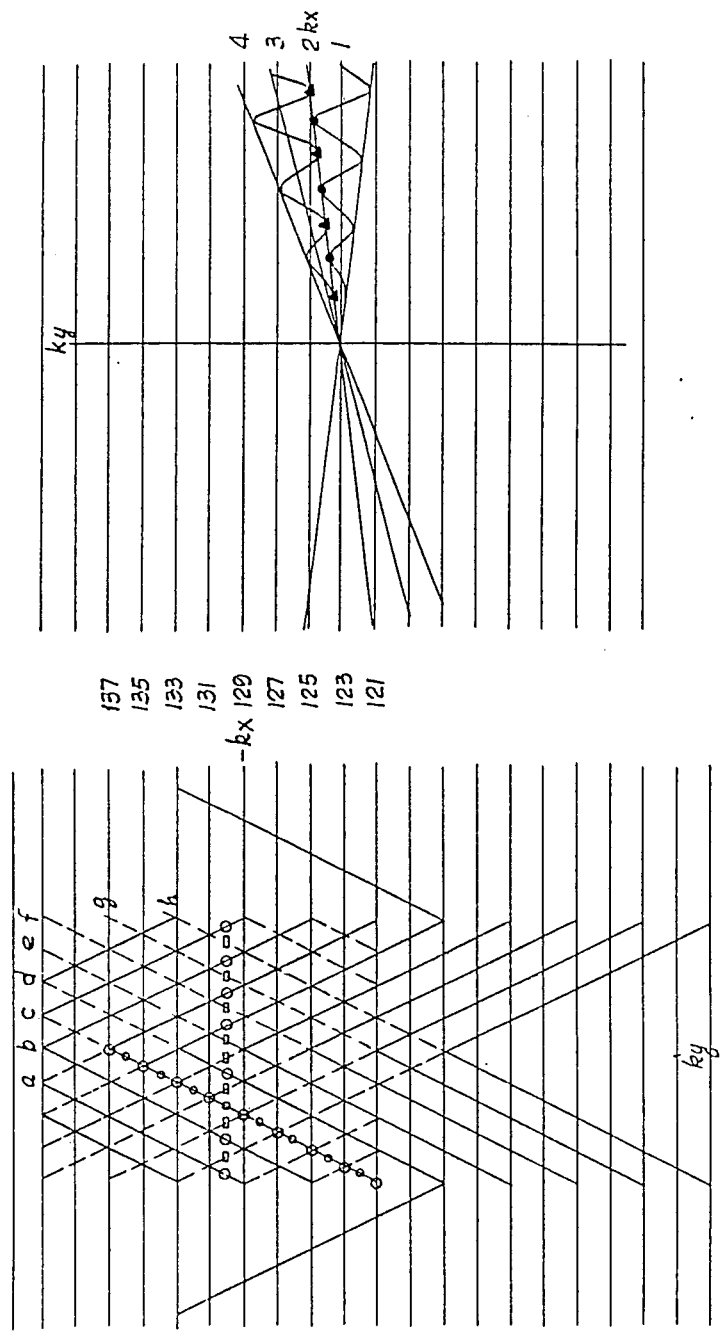

MAGNETIC RESONANCE IMAGING METHOD

DESCRIPTION

1. Technical Field

The invention relates to a magnetic resonance imaging method and apparatus to speed image data acquisition.

2. Background Art

Magnetic resonance imaging procedures are used to noninvasively produce medical diagnostic information. With such a procedure a patient is positioned in an aperture of a large annular magnet. The magnet produces a strong and static magnetic field which forces hydrogen and other chemical elements in the patient's body into magnetic alignment with the static field.

When diagnostic information is to be produced a series of radio frequency (RF) pulses are applied to the static magnetic field. These RF pulses are at the resonant frequency (Larmor) of the chemical element of interest. For human diagnosis with currently accepted procedures the RF pulses are at the resonant frequency of hydrogen which is abundantly present in a human because of the high percentage of water in a body. The RF pulses force the hydrogen molecules from their magnetically aligned positions and cause the molecules to precess or "wobble" in a motion akin to that of a spinning top as it is reaching the conclusion of a spin. This molecular precession is sensed to produce image signals, known as free induction decay signals, that are used to create diagnostic images.

In order to create an image of a plane of patient cross-section, it is necessary to differentiate between hydrogen molecules in the plane and those in other regions. Gradient fields are superimposed on the high strength static field for the accomplishment of this differentiation. Gradient coils are also pulsed to produce magnetic flux orthogonal to the static field. These gradient fields are applied after the initial RF pulse and change the resonant frequency of hydrogen molecules within the image plane to map the spatial frequency domain content of patient structure onto the free induction decay signal. By varying these gradient fields (read gradients) in a controlled manner sufficient free induction decay data is obtained to image the patient.

Free induction decay signals from a region of interest are sensed and Fourier transformed in accordance with known imaging techniques to provide an image of structure variation within the body. Two dimensional Fourier transform (2DFT) magnetic resonance imaging techniques presently take on the order of minutes from the beginning of data acquistion to the formation of an image. This time is needed to maintain optimum signal-to-noise, resolution, and contrast in the images. Many sets of data under a variety of conditions (varying the RF signal repetition time and the spin-echo time) must be collected to accurately extract information on spin-density and relaxation times. These time constraints restrict patient throughput even if all other steps of magnetic resonance imaging are performed as efficiently as possible.

Standard two dimensional Fourier transform imaging techniques utilize a phase encoding grandient, $G_y$, that is varied from one view to the next unitl N views of data are collected. The time required to acquire sufficient data is proportional to the data repetition rate times the number of views. For a one second repeat time with 256 views and an averaging of two data runs per view, the data acquisition time alone is over 8 minutes.

An alternate gradient encoding scheme proposed by Manfield and Pykett is discussed in an article entitled "Biological and Medical Imaging by NMR", Journal of Magnetic Resonance 29,355–373 (1978) and is known as echo-planar imaging. The theory behind echo-planar imaging is to modulate or oscillate the gradient field in such a way that enough information is obtained to image a planar slice of a subject in a single data acquisition sequence. This echo-planar technique has clear advantages in speed since the time for producing an image can in theory be reduced from many minutes to a few seconds.

With the present magnetic resonance imaging hardware the echo-planar technique places severe demands on gradient field strength. For a normal high resolution image ($\sim 1$ mm resolution) using this technique the existing gradient field producing hardware falls short in field strength by an order of magnitude. This discrepancy cannot be overcome by fine tubing gradient coil energization circuits.

In order to overcome these hardware imitations the oscillating frequency can be reduced as taught by Young and Burl (U.S. Pat. No. 4,355,282). This modified Echo-Planar technique is not able to collect all the data in a single view. Also, the resolution of this technique is hardware limited.

It has been proposed by C. M. J. Van Uijen that a combination of two dimensional Fourier Transform and echo-planar imaging phase encoding be used to reduce magnetic resonance imaging scan times. Note U.S. Pat. No. 4,527,124, issued July 2, 1985 to C. M. J. van Uijen. The perceived advantage of this proposal is a lowering of gradient amplitudes so that encoding is more feasible than the echo-planar technique. Use of lower amplitudes makes this proposal slower than the proposed echo-planar technique, were it achievable, yet faster than traditional two dimensional Fourier Transform imaging.

The Van Uijen proposal is inflexible in that a specific constant amplitude and frequency of gradient oscillation is required. In this regard, the proposal is similar to echo planar proposals. If the amplitude and frequency achievable with the field producing hardware varies from the specified values the technique is unsuitable. Experience with magnetic imaging hardware indicates that this is the case for high resolution imaging. Thus, to applicants knowledge, the Van Uijen proposal has never been successfully implemented in any magnetic Resonance Image Scanner.

DISCLOSURE OF INVENTION

Practice of magnetic resonance imaging with the present invention collects data with fewer views than prior art procedures used to produce clinically useful diagnostic images. This is accomplished with comparable image quality.

In accordance with a preferred imaging method a subject of interest is placed within a relatively high strength uniform magnetic field to align magnetic moments within the subject. An excitation signal re-orients these magnetic moments and during a relaxation period a transition of these moments back to an initial condition is monitored. A phase encoding is performed by applying a gradient field in the form of a fixed amplitude pulse along y. This is followed by a read gradient consisting of an oscillating field along y and static field along x.

As in the prior art, these imaging steps are repeated until sufficient data is obtained to create an image of structure variation in the subject. The magnitude of the fixed amplitude pulse is sequentially changed while the magnitude and frequency of the oscillatory field is maintained constant as is the static field along x. The number of data acquisition sequences required with the procedure is reduced and the amount of this reduction varies with the magnitude of the oscillating gradient field since this determines how quickly the object's spatial-frequency domain is mapped onto the free induction decay signals from the cross section of interest.

Unlike the other techniques, practice of the invention is not critically dependent on achieving a specific amplitude or frequency of oscillation in the encoding field. If the oscillations vary from an optimum in either amplitude or frequency special filtering steps are performed to take these variations into account. These corrections assure effective uniform signal coverage in Fourier (K) space. If the frequency of encoding oscillation is varied from a theoretical optimum a different rebinning procedure than would be used with the optimum is applied to the data. If the amplitude is not ideal, an amplitude correction is applied. Implementation of a generalized frequency and amplitude makes the present method useful whereas the Van Uijen proposal with its inflexible approach to oscillating gradient field encoding is believed to be impractical.

Preferred amplitude and frequency corrections are presented below. Briefly, these correction re-organize the free induction decay data in a manner to approximate data that would have been obtained if the amplitude and frequency has conformed to optimum levels and rates. These corrected values are obtained by a specific filtering so that the spatial-frequency domain (K-space) is uniformly covered. Then the second transform is applied to the data in accordance with known procedures (typically Fourier transformed) to obtain a spatial mapping of spin densities within the object.

The frequency of phase encoding oscillation is, in accordance with one aspect of the invention, intentionally varied (not within a given scan but in a different experiment relative to the first) until reasonable coverage of K-space occurs. This makes the image less sensitive to magnetic field inhomogeneities by allowing an increase in the static portion of the read gradient ($G_x$). The prior art, with its teaching of strict adherence to well defined frequency and amplitude for phase encoding does not countenance such a solution to the field inhomogeneity problem. Indeed, by changing the frequency of the oscillating field, a natural adjustment occurs in its amplitude in k space.

Practice of the invention results in a time savings in data acquisition without a loss in resolution and therefore constrast of magnetic resonance images. Resolution can be continually improved along one axis (y) by merely collecting more views without any further limitations. These and other advantages of this method will become better understood when a detailed discussion of a preferred embodiment of the invention is described in conjunction with the accompanying drawings.

BRIEF DESCRIPTION OF THE DRAWINGS

FIG. 1 is a perspective schematic of a magnetic resonance imaging scanner;

FIG. 1A is a perspective schematic of gradient coils for phase encoding a subject region of interest;

FIG. 2 shows a standard 2DFT spin echo sequence with five values of $G_y$, an encoding gradient represented by five separate phase encoding increments along $G_y$;

FIG. 3 shows that a coverage of data (Fourier or k) space prior to signal sampling is limited to lines parallel to the $k_x$ axis and of limited extent ($\pm N\Delta t/2$) where N is the total number of sample points;

FIG. 4 shows uniform coverage of data space in $k_x$ and $k_y$ with uniform data sampling;

FIG. 5 shows an example of a hybrid sequence with three lines of phase encoding increments shown along $G_y$ to illustrate that less views are taken than in the FIG. 2 sequence;

FIG. 10 shows hybrid data filtered after a first FFT as it would appear after performing an inverse fast Fourier transform;

FIG. 11 shows an alternate hybrid encoding sequence;

FIG. 12 shows a coverage in data space for an example low frequency hybrid technique; and FIG. 13 shows a volume imaging encoding sequence.

FIG. 14 shows an alternate coverage of data space using an extra scan to reduce noise from nonuniform sampling.

FIG. 15 shows a hybrid approach to projection reconstruction.

BEST MODE FOR CARRYING OUT THE INVENTION

Figure 6:
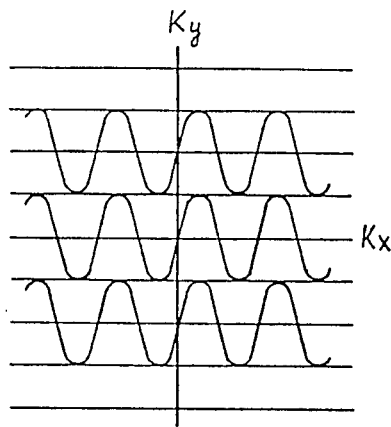
FIG. 6 shows data space coverage prior to sampling of the FIG. 5 sequence.

Turning now to the drawings, FIG. 1 shows a magnetic resonance scanner 10 having a large encircling magnet 12 for generating magnetic fields within a patient aperture 14. Shown in proximity to the magnet 12 is a patient couch 16 having a headrest 18. A patient is positioned on the couch 16 in a prone position and then moved into the patient aperture 14 for magnetic resonance scanning.

During a head scan a probe coil or resonator 20 is moved on rollers 22 so that the patient's head is positioned within the coil 20. With the probe coil 20 encircling the patient's head, the coil is energized with a high frequency signal which sets up a time varying magnetic field in the region of interest. Various techniques are known within the art for pulsing the probe coil in ways to produce meaningful resonance information which can be utilized in imaging. The probe coil 20 also monitors signals from the patient as magnetic moments decay from an excited to steady state condition. Gradient coils 30 (FIG. 1A) also encircle the patient to produce gradient fields $G_x$, $G_y$, $G_z$ which in combination with the high strength field of the magnet 12 selectively focus on particular patient regions. Additional details regarding a magnetic resonance scanner configuration are disclosed in U.S. Pat. No. 4,355,282 to Young et al which is incorporated herein by reference.

Prior art magnetic resonance imaging sequences are based on two dimensional Fourier transform (2DFT) phase encoding techniques. An example sequence for planar excitation of a spin-echo $\tau$ scan is shown in FIG. 2. A phase encoding gradient, $G_y$, is varied from one view to the next and N views of data are collected. A 2DFT reconstruction algorithm is then applied.

The signal sensed by the probe coil 20 can be expressed as a function of time t (centered at an echo position) and the view number of the value of the phase encoding gradient $G_y$. The signal for the ideal planar case (no change in spin-density over the z-direction for a given point (x,y) in the plane) is proportional to $$s(k_x,k_y) = \int\int_{-\infty}^{\infty} \rho(x,y,t) e^{-i(k_x x + k_y y)} dx dy \quad (1)$$

$$k_x = 2\pi\gamma \int G_x(t) dt \quad (2)$$

$$k_y = 2\pi\gamma \int G_y(t) dt \quad (3)$$

and $\gamma$ is the gyromagnetic ratio in Hz/Gauss. Here $\rho(x,y,t)$ is a product of the spin-density of the element of interest $\rho(x,y)$ times a function f(t) which depends on the relaxation time parameters and the system parameters such as $\tau$ and $t_{rep}$. Consider first the static phase encoding gradient along y. For simplicity, for times prior to data acquisition assume $G_y(t) = G_y = n\Delta G_y$ where n is the view number (centered about zero) and $\Delta G_y$ is the phase encoding increment from view to view. If this gradient is on for a time $t_y$, one finds $$k_y = 2\pi\gamma n \Delta G_y t_y. \quad (4)$$

One also takes $G_x(t) = G_x$ during the read portion of the gradient and $t = m\Delta t$ so that $$k_x = 2\pi\gamma G_x m \Delta t. \quad (5)$$

It is also necessary to assume that no motion occurs so that no phase information is distorted.

Given the above approximations and notation one may write the signal $$s(k_x,k_y) = \int\int_{-\infty}^{\infty} \rho(x,y) e^{-i(k_x x + k_y y)} dx dy. \quad (6)$$

In some cases it might be more transparent to represent the signal by $s(t,G_y)$ or $s(m,n)$ before or after sampling has occured. It is clear from this equation that the prior art coverage of data space is uniform when t is sampled uniformly. The Fourier (data) space coverage before and after sampling is shown in FIGS. 3 and 4, respectively.

The values of $\Delta G_y$ and $\Delta t$ are obtained from the Nyquist relations:

$$\Delta G_y = \frac{1}{\gamma t_y L_y} \quad (7)$$

and $$\Delta t = \frac{1}{\gamma G_x L_x} \quad (8)$$

where the Nyquist frequency is $$\omega_N = \pi \gamma G_x L_x. \quad (9)$$

One normally chooses the field of view so that $L = L_x = L_y$. These conditions must also be obeyed in the final equivalent coverage of k space in the present technique if the same resolution is to be retained as in the above 2DFT sequence.

In one imaging sequence used by the assignee of the invention, the sampling interval is 80 μs giving a Nyquist frequency of 6.25 kHz. The field of view for body images is 45 cm, giving a value of 0.0654 G/cm for the read gradient $G_x$. The value of $G_{ymax}t_y = 128 \Delta G_y t_y$ for the same field of view is 0.669 G.ms/cm and for $t_y = 3.5$ ms this gives $G_{ymax} = 0.191$ G/cm. The values of the gradients are scaled by 1.5 for head images where the field of view is 30 cm in each direction. In theory, the resolution attainable is roughly 1.2 mm for head images and 1.8 mm for body images.

Figure 7:
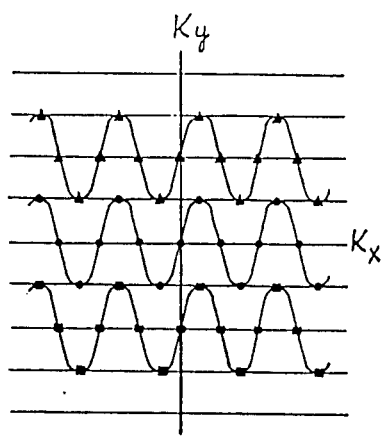
FIG. 7 shows data space coverage after uniform sampling.

The aim of the present hybrid imaging method is to collect the data faster by taking fewer views and yet retain the same amount of information as in the standard 2DFT approach. This is accomplished by oscillating the phase encoding gradient after the initial phase encodement. An example hybrid sequence of the invention is shown in FIG. 5. For a time savings of 2, the corresponding coverage of of Fourier space before and after sampling is illustrated in FIGS. 6 and 7, respectively. Looking at FIG. 7, one sees that, by oversampling each view by a factor of two, the same number of data points (in Fourier space) are covered as in FIG. 4. By oversampling, the same number of data points are covered per reorganized view as in each of the views taken in a 2DFT scan. The difference is that the sampled points in every other view are shifted by one-half a sampling interval. Half as many views are required and yet Fourier space is effectively covered as in the 2DFT case. This allows the identical resolution calculated above to be obtained by practice of the invention.

The hybrid sequence (FIG. 5) differs fundamentally from the standard sequence in that the increment of the phase encoding field $G_y$ from view to view is larger by a factor of q, where q is a positive integer less than or equal to N in a prior art 2DFT scan. First, the modified size of the steps between views is defined as $$\Delta G'_y = q \Delta G_y. \quad (10)$$

Second, the amplitude of the oscillating gradient should be such that the phase at one-quarter of a period is equal to what it would have been q/2 views away at that time in a 2DFT sequence. For example, for sinusoidal modulation of frequency $\omega$ and amplitude $G_o$, $$G_y(t) = G_o \cos \omega t. \quad (11)$$

The above restriction on the phase then gives $$\int_0^{T/4} G_y(t) dt = q \Delta G_y t_y / 2 \quad (12)$$

which upon integrating and rearranging gives $$G_o = \omega q \Delta G_y t_y / 2 \quad (13)$$

where $\omega = 2\pi/T$ is the frequency of oscillation and $G_o$ is the maximum amplitude of oscillation. According to FIG. 7, the frequency is such that one-half the period occurs in one sampling interval or $$\omega = \pi / \Delta t. \quad (14)$$

This is the ideal frequency of oscillation. Substituting Eq. (14) into Eq. (13) and using the Nyquist relations gives $$G_o = q\pi G_x L_x / 2L_y \quad (15)$$

and for $L_x = L_y$, $$G_o = q\pi G_x / 2.$$

For $q=2$, and a frequency of 2 kHz one has $\Delta t = 250$ $\mu s$, $G_x = 0.0209$ G/cm and $G_o = 0.0657$ G/cm. It has been found empirically that the system amplitude inputs must be larger than this by nearly a factor of two to actually attain this value. The reason for this is believed to be the eddy currents created when driving the oscillations at these large amplitudes and frequencies, further, the hardware limits how large q can be for an untuned gradient coil circuit and the amplifiers also limit how large q can be made.

At these read gradient values, the present technique is very susceptible to static field inhomogeneities. If the size of the object in the read direction is $c_x L$, then the read gradient could be increased by a factor of $1/c_x$ to improve resolution. Then, for display purposes, the image can be reduced to its proper dimensions.

Assuming that the correct amplitude of oscillation is available, an additional difference between hybrid and prior art 2DFT imaging is that the data must be oversampled by a factor of at least q for each view. For $q=2$, the oversampled data of each view must be reorganized between three adjacent views. This reorganization is performed by taking each even point of the nth hybrid view and associating it with each point in the 2nth 2DFT view as shown by the circles along the $k_x$ axis in the central row of FIG. 7. Each peak of the nth hybrid row is associated with every other point in the $(2n+1)$th 2DFT view and each valley is associated with every other point in the $(2n-1)$th 2DFT row as shown in FIG. 7. So for the odd rows (taking the central row as even) the data are effectively uniformly sampled but with each even point (the first point to the right of the $k_y$ axis being even) coming from the view below it and each odd point coming from the view above it. This is shown by the circles and triangles, respectively, of the first row above the $k_x$ axis in FIG. 7.

Mathematically, if the sampled data for the $q=2$ hybrid technique are represented by the array $s(m,n)$ then the reorganized data will be $s'(m',n')$. Where $$-M \leq m' \leq M \quad (16)$$

$$-N \leq n' \leq N$$

and $$-2M \leq m \leq 2M \quad (17)$$

$$-N/2 \leq n \leq N/2.$$

The relation between $s(m,n)$ and $s'(m',n')$ is as follows:

$$s(m,n) = s'(2m', n'/2) \text{ for even } n \quad (18)$$

$$= s'\left(2m' - 1, \frac{n'-1}{2}\right) \text{ for odd } n$$
$$\text{even } m$$

$$= s'\left(2m' - 1, \frac{n'+1}{2}\right) \text{ for odd } n$$
$$\text{even } m.$$

These relations become increasingly complex for higher q values and need to be expressed so as to recover s' from s.

For the general case we have the equality $$s(m,n) = s'(m',n') \quad (19)$$

where the points are sampled in such a way that they lie exactly on the corresponding 2DFT view. Eq. (16) is still valid, but Eq. (17) becomes $$-qM \leq m \leq qM \quad (20)$$

$$-N/q \leq n \leq N/q.$$

Table 1 illustrates how to convert from the oversampled data to pseudo-2DFT sampled data for positive m. The pseudo prefix here means that further data manipulation may be required. The following relationships do not depend on the type of modulation of $G_y(t)$, i.e., sinusoidal versus triangular, as long as data space is covered as in FIG. 7. One defines $p = 1 + q/2$ and mod-$(a,b) = a - b[a/b]$ where [ ] means integer part. For $a < 0$ one must replace mod(a,b) with mod(a,b)+q.

TABLE 1

| m' | n' | $\left[\frac{2m}{q}\right]$ | $\left[\frac{m}{q}\right]$ |
|---|---|---|---|
| $\left[\frac{m + q/2 - 1}{q}\right]$ | nq + mod(m,q) | even | even |
| $\left[\frac{m + q/2 - 1}{q}\right]$ | (n + 1)q − mod(m,q) | odd | even |
| $\left[\frac{m + q/2 - 1}{q}\right]$ | nq − mod(m,q) | even | odd |
| $\left[\frac{m + q/2 - 1}{q}\right]$ | (n − 1)q + mod(m,q) | odd | odd |

This table can be generalized for any frequency of oscillation. It is easiest to put in practice when the frequency is an integer multiple of the ideal frequency, $\omega$ or when it is smaller than $\omega$ by an integer factor.

The rebinning of the data is done as described above so that each new rebinning view has the same number of points. As the frequency of oscillation is reduced (as in FIG. 12) the rebinning procedure becomes more complicated in that each hybrid view has points associated with more normal 2DFT views. In general, starting from a minimum for a given hydrib view, each sampled point is associated with a higher view in normal data until the peak is reached, then each point is associated with a lower view (by 1 unit) until a minimum is reached and the process is repeated until all data is sorted. The edges of data space can be filled in by taking extra views or by phase shifting again (as described below) to effectively recenter the shifted data. The latter approach only slightly degrades resolution, the former does not.

Once the data are reorganized, the next step is to shift the even rows (odd n) to the right so that all the points for a given m (time point) lie in the same column. This is accomplished by implementing a data filtering operation.

First, one writes $$g(f) = \int_{-\infty}^{\infty} g(t)e^{-i2\pi ft} dt \quad (21)$$

where g(t) could be the signal for example. The Fourier transform of the function g(t+aΔt) is then $$g_a(f) = \int_{-\infty}^{\infty} g(t + a\Delta t)e^{-i2\pi ft} dt \quad (22)$$

$$= e^{i2\pi fa\Delta t} \int_{-\infty}^{\infty} g(t')e^{-i2\pi ft'} dt' \quad (22)$$

$$= e^{i\pi f\Delta t} g(f)$$

when a=½ (since q=2). This is equivalent to filtering the function g(f) by multiplying g(f) with $e^{i\pi f\Delta t}$ or, in a discrete case where f equals mΔf=m/2MΔt and 2 M is the number of sampled points.

$$g_a(f) = e^{i\pi m/M} g(f). \quad (23)$$

Figure 8:
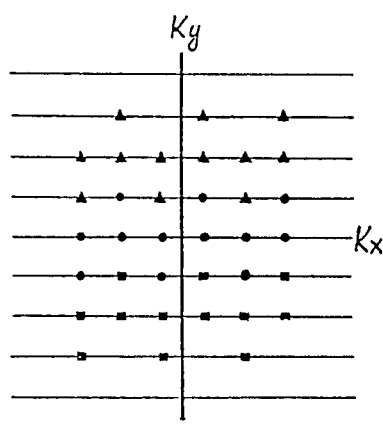
FIG. 8 shows hybrid data filtered after a first (fast) Fourier transform as it would appear after performing an inverse (fast) Fourier transform.

This is equivalent to having started with data sampled as in FIG. 8. After the data has been reorganized and the filtering has been applied, a normal 1DFT reconstruction algorithm can be used to form an image.

In summary, the hybrid technique consists of phase encoding the data with constant and oscillatory gradients. The data must be reorganized or rebinned so that a 2DFT type reconstruction is possible. Before the image can be reconstructed, the data must be filtered after the first Fourier transform.

If the frequency is not ideal, a new resorting algorithm is required, and if the amplitude is not ideal, an amplitude correction must also be applied. These procedures allow the present procedure to be implemented whereas the Van Uijen proposal will fail.

AMPLITUDE COMPENSATION

With presently available gradient coil drive circuits, it may be difficult to attain the desired amplitude for q=2, 2 kHz head data. The gradient coil system has a low Q and a broad frequency response. This allows the shaping of the phase encoding gradient to be facilitated but makes it difficult to drive the system at 2 kHz with large amplitude.

Figure 9:
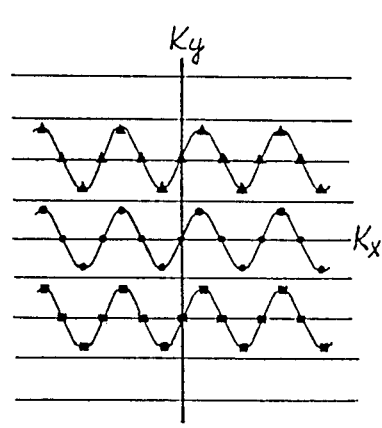
FIG. 9 shows sampled hybrid data for a non-ideal amplitude of oscillation with coverage of data space now highly non-uniform.

It is possible to overcome the problem of insufficient amplitude. If the oscillations are deficient in amplitude as in FIG. 9, after applying the data shift filter described above, the coverage of Fourier space is as in FIG. 10. The reconstructed image from this data set has aliased images or ghosts in the frequency direction. The coverage of Fourier space depicted in FIG. 10 must be made uniform as in FIG. 8.

Uniform coverage is obtained by breaking up the columns into two sets of uniformly spaced samples. The two data sets are formed by first selecting all even sampled points and filling the void of the odd points with zeros and second, selecting the odd points and filling the void of even points with zeros. These two data sets are transformed separately. Take the signal for a column to be g(t) and for the column split into even and odd parts as $g_e(t)$ and $g_o(t)$, respectively. Note that t is the phase variable. Once again, we take the central point to be even. The discrete transform of each of these functions [$g_e(f)$ and $g_o(f)$] will have aliased contributions which, for ideal amplitude, will cancel when the transforms are added together. Let the actual amplitude be γ=1+a times the ideal amplitude and Δt'=2Δt. If $$g(f) = \Sigma_{n'} g(t_{n'}) e^{i2\pi ft_{n'}} \quad (24)$$

then for the even function, $t_{n'}=n'\Delta t'$ and $$g_e(f) = g(f-f_N) + g(f) + g(f+f_N) \quad (25)$$

while for the odd function, $t_{n'}=(n'+\gamma/2)\Delta t'$, and $$g_o(f) = e^{-i\pi\gamma} g(f-f_N) + g(f) + e^{i\pi\gamma} g(f+f_N). \quad (26)$$

For positive f only the right hand two terms contribute so that $$g(f) = \frac{g_e(f) + e^{-i\pi a} g_o(f)}{1 + e^{-i\pi a}} \quad (27)$$

while for f negative only the left two terms contribute, so that $$g(f) = \frac{g_e(f) + e^{-i\pi a} g_o(f)}{1 + e^{-i\pi a}}. \quad (28)$$

This technique can be extended to any number of nonuniformly spaced points.

In implementing these corrections, the value for "a" must be negated from one column to the next (see FIG. 10). Also, to retain the same normalization, as in the case when a normal transform based on Δt is performed, g(f) in Eq. (28) must be multiplied by 2.

These expressions are not quite complete since the odd points are stored as if their amplitudes were correct. This problem is corrected if we replace $g_o(f)$ in Eq. (27) and Eq. (28) by $$g_o'(f) = e^{i\pi ma/M} g_o(f) \quad (29)$$

where $g_o(f)$ is the Fourier transform of the odd portion of a sampled column. This technique can also be used to center the data in k space, i.e. used as a calibration technique. This is done by shifting the starting sampling point and using the above technique so that no aliased information appears.

The effect of the oscillating amplitudes, filtering, and amplitude corrections is to take coherent noise and make it incoherent as well as causing the noise to be distributed throughout the image. The is advantageous especially when periodic motion of the object being imaged occurs. For example, eye motion causes noise to be distributed in the phase encoding direction throughout the vicinity of the eyes. This does not occur with the present hybrid method. In general, the integrated phase encoding noise which only occurs in the region of the object being imaged, is more uniformly distributed throughout the field of view. This can improve the background noise in the image noticeably. However, noise can also occur in the form of uncorrected aliased images.

Implementing the amplitude correction is done by first filtering with the inverse Fourier transform in Eq. (23) along the rows and then performing a Fourier transform. The data space coverage will then be as if the data had been taken as that illustrated in FIG. 10. In this state, it is then possible to perform the column (phase encoding) Fourier transform with the amplitude corrections. Then the row (time domain) transform is done again. The reorganization, filtering and the two extra Fourier transforms all increase the reconstruction time of an image but allow non-optimum amplitude gradient fields to be used.

OTHER APPROACHES

The present implementation of the q equal to 2 hybrid technique results in a low read gradient of 0.02 G/cm to attain an ideal amplitude. This low gradient is sensitive to field inhomogeneities. The possible solutions to this sensitivity include: first, increasing the available voltage by adding gradient amplifiers in series to the present configuration; second, tuning the gradient coil circuit; or third, developing a low frequency hybrid technique.

Each of these solutions would allow a smaller $\Delta t$ and, therefore, a larger read gradient to be used. The second solution has been successfully employed in echo planar experiments. Even doubling the present voltage capabilities would only allow a factor of 1.4 increase at 2 kHz in the read gradient, nevertheless, this increase helps overcome field inhomogeneities. Another approach is to allow a larger read gradient to fill image space and then reduce the image to its proper proportions. On bodies and heads this can gain another factor of 1-2. Although this will introduce an increase in the noise, the resolution should significantly improve. Also, with ideal amplitudes, the reconstruction is considerably simplified and faster.

The first two field inhomogeneities solutions also allow for higher frequency hybrid methods. For example, doubling the ideal frequency and changing the signal sampling permits data from all views spanned to be collected at once. No view intermixing need occur. This implies that q takes on odd values. If the oscillations cover plus or minus one view, then $q = 3$, i.e., a factor of three savings in time is realized.

One of many possible alternate scans is illustrated in FIG. 11. The coverage of k-space is such that small errors in sampling affect the image less, although signal to noise is still increased by more than $\sqrt{q}$. Signal-to-noise is a maximum when triangular coverage of k-space is used; i.e. the loss is only $\sqrt{q}$ compared to normal 2DFT imaging. For sinusoidal oscillations the loss is $(1 + \pi g/2)^{\frac{1}{2}}$ so that the analog bandwidth of the filtered data prior to processing must be increased by the same factor.

LOW FREQUENCY TECHNIQUE

The third solution involves lowering the frequency. If the frequency is one-half the ideal frequency, then the coverage of data space, for $q = 2$, will be as shown in FIG. 12. Note that twice the amplitude of the oscillating gradient in k space is required as is seen in FIG. 12. However G need not be changed if q is unchanged (see eq. 13). It is now possible to overcome amplitude and eddy current problems because a lower frequency is being used.

In summary, low, ideal and high frequency hybrid techniques are possible. Data reorganization is facilitated by using integer multiples of $\omega$ for high frequencies and integer divisors of $\omega$ for low frequencies. Until sufficient gradient amplifier voltage and currents are available, it is necessary to use the latter approach. This will consist of correcting for non-ideal amplitudes and data reorganization, the former being the most difficult.

VOLUME HYBRID

Another use of the invention is for volume imaging. In this case, noise will be so low that any increase by a factor of $\sqrt{2}$ or 2 will not be of consequence. Being able to maintain resolution but decrease data collection times by factors of 2 and possibly much more will make volume imaging a viable technique. A sequence is shown in FIG. 13. Here a selective 90° pulse along z and a selective 180° pulse along y are used to excite a rectangular strip along x. Filtering the signal will then allow various sizes of the strip to be isolated while a frequency offset would allow the center of the volume of interest to be shifted. The oscillation of both z and y gradients allows information from as many as nine rows in k-space to be collected. This leads to data being collected four times faster than a normal 2DFT sequence, although only effective $q = 2$ coverage in each direction is applied. The previous techniques can be extended to any value of q in either direction. This reduces to the planar hybrid volume coverage when $q = 1$ in one direction.

Planar volume means that each data acquisition proceeds as in the two-dimensional example in that the oscillating gradients are applied parallel to only one of the phase encoding gradients. In this case, no new rebinning algorithms are required.

DOUBLE COVERAGE

The noise in the image in the hybrid method can be reduced by obtaining more uniform coverage of data space initially. The optimum example is triangular oscillations leading to triangular coverage. If a second scan is run where the oscillations are 180° out of phase with the first, then it is possible to extract uniformly covered rows of data, filter the data and recover, with no loss of S/N due to processing, equivalent uniform coverage in columns. Although a loss of 2 in time results, making the effective $q = q/2$ most scanning procedures already acquire 2 sets of data for averaging purposes. The same approach can be used with sinusoidal oscillations to improve the coverage.

A portion of data space for q and m both equal to 4 is shown in FIG. 14. The circles along line "c" represent normally sampled points properly rebinned. The circles and squares along row 130 have also been rebinned. Further rebinning is required as discussed below.

The data are now rebinned as before for each of the two scans. Then every other set of m points in a given row are separated and replace their counterparts in the opposite row. This replacement then gives exact uniform row coverage in the triangular case as described earlier. The first transform is applied to each data row, properly filtered, and the data added together. The second transform is then applied. FIG. 14 shows th splitting into two sets of 4 for row 130. Note the 4 parallel lines a, b, c and d from the first data set (solid lines) and the 4 parallel lines e, f, g and h from the 180° shifted data set (dashed lines).

Note that from row 130 the first 4 circles are taken then the last 4 squares to give the first new rebinned data row. The remaining points form the second new row. This procedure is applied throughout data space.

PROJECTION RECONSTRUCTION

Unlike 2DFT, projection reconstruction has no phase encoding gradient. Instead, data space is covered by varying the ratio of the $G_x$ and $G_y$ read gradient components from scan to scan. This variation can be parameterized by the angle, $\theta$ made with the $k_x$ axis. A partial normal coverage is illustrated in FIG. 15 by the solid lines. A complete coverage usually has the radial lines uniformly spaced in $\theta$ with increments $\Delta\theta$. Once again by oscillating the gradients (this time both $G_x$ and $G_y$) and sampling faster, it is possible to acquire a complete coverage of data space q times faster. In this case, the time modulations are more complicated than before. The data must be similarly rebinned and filtered prior to reconstruction.

As before, it is possible to use the low frequency technique to overcome hardware limitations.

The example illustrated in FIG. 15 is q equal to 2 and m equal to 1. The rebinning takes place as described earlier with respect to FIG. 7.

GENERAL TECHNIQUES

Applications to other techniques such as circular coverage, spiral coverage, etc. is equally applicable. Certain gradients are oscillated, data are rebinned, filtered, and appropriately reconstructed.

The values of $k_x$ and $k_y$ for projection reconstruction are $$k_x(\theta,t) = 2\pi\gamma x\, G_x t$$

$$k_y(\theta,t) = 2\pi\gamma y\, G_y t$$

Here the read gradient for a given view is $$\vec{G} = (G_x, G_y)$$
$$= G(\cos\theta, \sin\theta).$$

To obtain the hybrid coverage $G_x$ and $G_y$ are time modulated so that:

$$\int G_x(t)dt = Gt \cos(\theta+\alpha)$$

$$\int G_y(t)dt = Gt \sin(\theta+\alpha)$$

Here $\alpha$ varies from 0 to $\Delta\theta$ to 0 to $-\Delta\theta$ to 0 and repeats for q=2, m=1 coverage.

This can be effected by letting $G_x(t)$ and $G_y(t)$ be sinusoidally modulated and having the amplitude change from sampled point to sampled point to maintain the above relations. Other forms of modulation are also possible as long as the above relations remain valid.

The present invention is seen to be adaptible to many variations, all aimed at recovering the equivalent of uniform or sufficient Fourier space (or K space) data coverage at enhanced rates by use of a hybrid phase encoding procedure in order to maintain resolution. It is the intent the invention encompass all such variations, modifications and alterations falling within the spirit or scope of the appended claims.

We claim:

1. In a magnetic resonance imaging system, a method for scanning a subject comprising the steps of:

creating a relatively uniform magnetic field over a region of interest, said field tending to align magnetic moments within the subject;

applying one or more excitation signals a number of times in the form of a pulse of radio frequency energy to reorient magnetic moments within the region of interest;

applying one or more phase encode gradient field pulses in conjunction with said excitation signals to phase encode the region of interest, said gradient field pulses being changed for each repetition of said excitation signals;

subsequent to the phase encoding of said region, monitoring signals generated by magnetic moments within the region in at least one sampling period;

concurrently with the monitoring of magnetic moment generated signals, applying at least one oscillating gradient field having an amplitude and frequency which gradient field oscillates a plurality of times during the sampling period and applying at least one static gradient field;

reorganizing the monitored signals into a predetermined format;

multiplying the reorganized signals with a frequency dependent filter signal having a filter frequency and a filter amplitude which are selected in accordance with the oscillating gradient field frequency and amplitude; and, creating an image of internal structure of the subject in the region of interest.

2. The method of claim 1 additionally comprising the step of applying a localizing field gradient for choosing a cross-section of the subject.

3. A method of magnetic resonance imaging, comprising the steps of:

(a) creating a relatively uniform magnetic field over a region of interest, said field tending to align magnetic moments within the region of interest;

(b) applying a plurality of radio frequency pulses to reorient magnetic moments within the region of interest such that at least one echo signal is caused during a subsequent sampling interval;

(c) phase encoding said region of interest by applying at least one phase encode gradient field pulse along a first direction in conjunction with said excitation pulses, said phase encode gradient field pulses being altered in subsequent repititions of said excitation;

(d) during the sampling interval, applying a plurality of cycles of an oscillating frequency encode gradient field along the first direction, the oscillating frequency encoding field having a frequency encode gradient amplitude and a frequency encode gradient frequency;

(e) concurrently with applying the oscillating frequency encode gradient field, applying a static gradient field along a second direction;

(f) during the sampling interval and concurrently with applying the oscillating frequency encode gradient field, sampling the echo signal create sampled data values in a data space, which sampled data values are nonuniform in time in the data space;

(g) reorganizing the sampled data values into a predetermined format which substantially covers the data space;

(h) filtering the sampled data values in said data space to cause uniformity in sampled data coverage in the data space; and, (i) transforming the sampled data values to construct an image of structure variation within the region of interest.

4. The method of claim 3 wherein the first direction of the phase encoding pulses is orthogonal to the second direction of the static gradient field.

5. The method of claim 4 further including applying an additional phase encoding gradient along a direction which is orthogonal to the first direction prior to applying the oscillating frequency encoding gradient field for volume imaging of the region.

6. The method as set forth in claim 3 wherein the reorganizing step includes reorganizing the sampled data values into a plurality of data sets; and, wherein the filtering and image creating steps and carried out separately on each data set; and, further including the step of adding the images constructed from each data set.

7. A magnetic resonance imaging method for constructing a mapping of structure variations in a region of interest of a subject comprising the steps of:

(a) creating an essentially uniform magnetic field over the region of interest that tends to align magnetic moments within the subject;

(b) imposing one or more localizing field gradients on the subject to select the region of interest to be mapped;

(c) applying at least one radio frequency pulse of energy to reorient magnetic moments within the region of interest such that an echo signal is caused by a transition of magnetic moments in the region of interest during a subsequent sampling interval;

(d) applying at least one phase encode gradient field to phase encode the region of interest;

(e) subsequent to the applying of the phase encode gradient field and during the sampling interval, frequency encoding the region of interest by applying at least one oscillating gradient field having an amplitude and frequency and applying a static gradient field orthogonal to the oscillating gradient field;

(f) during the sampling interval, sampling the echo signals a plurality of times during each of a plurality of cycles of the oscillating gradient field, each sampling producing a sampled data value;

(g) reorganizing the sampled data values to a nonuniform coverage in Fourier space;

(h) selecting a filter function in accordance with the frequency of the oscillating gradient field;

(i) filtering the reorganized sampled data values with the selected filter function to obtain an array of data values which is equivalent to a uniform array of data values which substantially uniformly covers a Fourier space without filtering; and, (j) transforming said reorganized and filtered sampled data values to a construct the mapping of structure within said region of interest.

8. The method as set forth in claim 7 wherein the step of applying at least one radio frequency pulse includes: applying at least one 90° excitation signal to cause nuclear magnetic moments within the region of interest to resonate; and, applying at least one 180° excitation pulse to cause the resonating nuclear magnetic moments within the region of interest to rephase into the echo signal.

9. The method as set forth in claim 8 further including repeating steps (c) through (f) a plurality of times each time with a different static gradient field in step (e).

10. The method as set forth in claim 7 wherein the step of applying at least one radio frequency pulse includes: applying at least one 180° radio frequency and at least one 90° radio frequency excitation pulse.

11. The method of claim 7 additionally comprising the step of applying a dephasing gradient in the same direction as and prior to the application of the frequency encoding gradient.

12. A magnetic resonance system for scanning a subject comprising:

(a) means for creating a relatively uniform magnetic field over the region of interest of the subject to align magnetic moments therein;

(b) means for exciting magnetic resonance such that at least one echo signal is produced during a subsequent sampling interval as magnetic moments within the region of interest re-orient;

(c) means for monitoring the echo signals during the sampling interval;

(d) gradient field generating means for first phase encoding said region of interest by applying one or more gradient field pulses in conjunction with the magnetic resonance excitation, and then applying at least one oscillating field gradient which oscillates a multiplicity of times at a field gradient frequency during the sampling interval;

(e) signal processing means for operating on the monitored echo signals with a filter function which has an oscillation frequency selected in accordance with the field gradient frequency; and (f) means for generating an image representation depicting internal structure of the subject in the region of interest from said filtered echo signals from the processing means.

13. The system of claim 12 wherein the gradient field generating means comprises means for simultaneously creating at least two mutually orthogonal phase encoding gradient fields, at least one of which is followed by the oscillating frequency encoding field gradient such that data characterizing a volume of said subject is obtained by said means for monitoring.

14. The system of claim 13 additionally comprising means to generate one or more localizing gradient fields.

15. The system of claim 12 where the gradient field generating means comprises means for creating a singular phase encoding gradient field preceding the oscillating frequency encoding field gradient so that data characterizing a cross section of a volume of said subject is obtained by said means for monitoring.

16. The system of claim 15 additionally comprising means to generate one or more localizing gradient fields.

17. In a magnetic resonance imaging system, a method for scanning a subject comprising the steps of:

(a) creating a relatively uniform magnetic field over a region of interest of the subject, said field tending to align magnetic moments within at least the region of interest;

(b) applying pulses of radio frequency energy to reorient magnetic moments within the region of interest;

(c) applying a phase encoding gradient field over at least said region of interest;

(d) applying at least one oscillating gradient field having an amplitude and frequency subsequent to the phase encoding gradient field to frequency encode at least the region of interest;

(e) concurrently with the applying of the oscillating gradient and over a plurality of cycles thereof, monitoring signals generated by the reoriented magnetic moments in the region of interest;

(f) reorganizing the monitored signals into a predetermined format in a data space;

(g) filtering the reorganized signals to compensate for at least one of the frequency and the amplitude of the oscillating field by transforming the reorganized signals to an equivalent of a uniform Fourier data space; and, (h) creating an image representation depicting internal structure of the region of interest from said filtered signals.

18. The method of claim 17 further including prior to step (d) adjusting the frequency of the oscillating gradient field to adjust resolution of the image representation.

19. The method of claim 17 further including prior to step (d) adjusting the timing of the monitoring step to calibrate the coverage of monitored signals in data space.

20. A method of magnetic resonance imaging, comprising the step of:

(a) creating a relatively uniform magnetic field over a region of interest of a subject, said field tending to align magnetic moments within the region of interest;

(b) applying a plurality of radio frequency pulses to reorient magnetic moments within the region of interest such that at least one echo signal is created during a subsequent sampling interval;

(c) phase encoding said region of interest by applying at least one phase encode gradient field pulse along a first direction in conjunction with said excitation pulses, said phase encode gradient field pulses being altered in subsequent repetitions of said excitation;

(d) during the sampling interval, applying at least one oscillating frequency encode gradient field along the first direction, each oscillating frequency encoding field having a frequency encode gradient amplitude and a frequency encode gradient frequency, the frequency encode field undergoing a plurality of oscillations during the sampling interval;

(e) concurrently with applying the oscillating frequency encode gradient field, applying one of a preselected plurality of static gradient fields along a second direction;

(f) during the sampling interval and over a plurality of oscillations of the frequency encode gradient field, sampling the echo signal to create sampled data values in a data space, which sampled data values are nonuniform in time in the data space;

(g) repeating steps (b) through (f) with the oscillating gradient field phase shifted to produce a second scan;

(h) reorganizing the sampled data values from the first and second scans to produce two data sets;

(i) reconstructing first and second images from the first and second data sets; and, (j) adding the first and second images together.

21. The method of claim 20 wherien the oscillating gradient fields are phase shifted by 180°.

22. A method of magnetic resonance scanning for examining a region of interest of a subject, the method comprising:

(a) disposing at least the region of interest in a relatively uniform magnetic field;

(b) exciting magnetic resonance of magnetic moments within the region of interest such that at least one magnetic resonance echo signal is generated during at least one preselected sampling interval;

(c) sampling the echo signals during the sampling interval to obtain data values in a data space;

(d) concurrently with the sampling of the echo signal, applying an oscillating gradient field such that the sampled data values are disposed along a corresponding oscillating path which oscillates about a horizontal row in through the data space, whereby the data values are in an inappropriate form for reconstruction with a Fourier transform algorithm which requires data values disposed along a regular, rectangular grid in data space;

(e) repeating steps (b) through (d), in each repetition applying a different gradient such that the data values from each repetition lie along generally oscillating paths which oscillates about parallel disposed horizontal rows in the data space, the static gradients being selected to be sufficiently small relative to an amplitude of the oscillation that at least adjacent oscillating paths are interleaved with data from a plurality of the oscillating paths being disposed in a common horizontal row;

(f) reorganizing the data values in data space into horizontal rows and generally vertical columns which are distorted in accordance with a frequency of the oscillating gradient field;

(g) operating on the data values in data space with a frequency dependent filter function whose frequency is selected in accordance with the oscillating gradient field frequency such that the columns are transformed into vertical columns, whereby a rectangular data space with vertical columns and horizontal rows is created.

23. The method as set forth in claim 22 further including:

(h) transforming the data values from the rectangular data space into an image representation depicting structure in the region of interest.

24. The method as set forth in claim 23 further including repeating steps (b) through (h) with an oscillating gradient field which is shifted by 180° to create a second image representation and adding the image representation.

25. The method as set forth in claim 22 wherein the data value oscillating paths are sufficiently interleaved such that data values sampled from at least three different echo signals are disposed in each horizontal row whereby coherent noise common to the echo signals is distributed among a plurality of rows.

26. The method as set forth in claim 22 wherein after operating on the data values with the filtering function, there are voids in the rectangular data space for which no data values exist and further including reorganizing the values in data space from each repetition into a plurality of superimposed rectangular data spaces, each of which is substantially complete;

transforming each rectangular data space separately into an image representation; and, combining the image representations.

27. A method of magnetic resonance imaging for imaging a region of interest within a subject, the method comprising:
   (a) immersing at least the region of interest in a substantially uniform magnetic field;
   (b) exciting magnetic resonance of at least selected magnetic dipoles disposed in the region of interest such that an echo signal is substantially caused during a preselected sampling interval;
   (c) during the sampling interval, applying an oscillating gradient field across the region of interest, whereby a data space representation of the region is frequency encoded;
   (d) sampling the echo signal during the application of the oscillating gradient field;
   (e) reorganizing the sampled echo signal to a predetermined format, whereby the data space representation of the region is reorganized; and,
   (f) filtering the reorganized signal to compensate for nonuniform encoding in the data space attributable to the oscillating gradient field and reconstructing an image representation of structure in the region of interest from the filtered signal.

28. The method as set forth in claim 27 further including the step of adjusting an amplitude of the oscillating gradient field to adjust coverage of the data space in time while maintaining a fixed resolution.

29. The method as set forth in claim 27 further including the step of adjusting a frequency of the oscillating gradient field to adjust image resolution.

30. A method for scanning a subject comprising the steps of:
   (a) creating a relatively uniform magnetic field over a region of interest;
   (b) exciting magnetic resonance at least within the region of interest;
   (c) monitoring signals generated within the region in response to the resonance excitation;
   (d) during the monitoring step, nonuniform frequency encoding said region of interest in a data space representation of the region;
   (e) reorganizing the monitored signals to a predetermined format;
   (f) filtering reorganized signals to compensate for nonuniform encoding in data space due to the frequency encoding; and,
   (g) creating an image representation depicting structure in the region of interest.

* * * * *